(12) United States Patent
Sun et al.

(10) Patent No.: US 10,907,114 B2
(45) Date of Patent: Feb. 2, 2021

(54) METHOD FOR CO-PRODUCTION AND PROCESSING OF BIOLOGICAL ENERGY SOURCES BY OIL CROPS

(71) Applicant: Jiangnan University, Wuxi (CN)

(72) Inventors: Fubao Sun, Wuxi (CN); Song Tang, Wuxi (CN)

(73) Assignee: Jiangnan University, Wuxi (CN)

( * ) Notice: Subject to any disclaimer, the term of this patent is extended or adjusted under 35 U.S.C. 154(b) by 160 days.

(21) Appl. No.: 16/395,824

(22) Filed: Apr. 26, 2019

(65) Prior Publication Data

US 2019/0249107 A1    Aug. 15, 2019

Related U.S. Application Data

(63) Continuation of application No. PCT/CN2017/117784, filed on Dec. 21, 2017.

(30) Foreign Application Priority Data

Dec. 30, 2016    (CN) .......................... 2016 1 1256701

(51) Int. Cl.

| C11B 1/04 | (2006.01) |
| C11B 1/10 | (2006.01) |
| C11B 3/00 | (2006.01) |
| C11C 3/04 | (2006.01) |
| C12P 7/46 | (2006.01) |
| C12P 7/10 | (2006.01) |
| C12P 7/18 | (2006.01) |
| C12P 7/28 | (2006.01) |
| C12P 7/52 | (2006.01) |
| C12P 7/64 | (2006.01) |
| C10L 1/02 | (2006.01) |
| C12P 7/36 | (2006.01) |
| C12P 3/00 | (2006.01) |
| C12P 5/02 | (2006.01) |
| C12P 7/16 | (2006.01) |

(52) U.S. Cl.
CPC ............... *C11B 1/04* (2013.01); *C10L 1/02* (2013.01); *C11B 1/10* (2013.01); *C11B 3/003* (2013.01); *C11C 3/04* (2013.01); *C12P 3/00* (2013.01); *C12P 5/023* (2013.01); *C12P 7/10* (2013.01); *C12P 7/16* (2013.01); *C12P 7/18* (2013.01); *C12P 7/28* (2013.01); *C12P 7/36* (2013.01); *C12P 7/46* (2013.01); *C12P 7/52* (2013.01); *C12P 7/649* (2013.01); *C12P 7/6436* (2013.01); *C12P 2201/00* (2013.01); *C12P 2203/00* (2013.01); *Y02E 50/10* (2013.01); *Y02E 50/30* (2013.01)

(58) Field of Classification Search
None
See application file for complete search history.

(56) References Cited

U.S. PATENT DOCUMENTS

| 2012/0167648 A1* | 7/2012 | Cantizani ................ C10L 1/026 71/11 |
| 2014/0235761 A1* | 8/2014 | Yoon ....................... C08L 99/00 524/15 |
| 2014/0325897 A1* | 11/2014 | Lihme ..................... C12P 7/649 44/307 |
| 2019/0161424 A1* | 5/2019 | Freeman .................. B01D 3/10 |

FOREIGN PATENT DOCUMENTS

| CN | 1821209 A | 8/2006 |
| CN | 103571615 A | 2/2014 |
| CN | 105602701 A | 5/2016 |
| CN | 106868051 A | 6/2017 |

OTHER PUBLICATIONS

Machine translation with Chinese text of CN 104862344 A (published Aug. 26, 2015) downloaded from Foreign Patent Finder from dialog on Nov. 13, 2020. (Year: 2015).*
Yoo et al. Appl. Biochem. Biotechnol. (2012) 166: 576-589 (Year: 2012).*
Harrington et al. J. Am. Oil Chem. Soc. (1985) 62(6): 1009-1013 (Year: 1985).*

* cited by examiner

*Primary Examiner* — Susan M Hanley
(74) *Attorney, Agent, or Firm* — IPro, PLLC

(57) ABSTRACT

The present invention discloses a method for co-production and processing of biological energy sources by oil crops, and belongs to the technical fields of oleochemical industry and biomass chemical industry. The method comprises the following steps: husking and drying oil crop seeds to obtain husks of which the moisture content is 5%-12% and oil seeds of which the moisture content is 30%-55%; squeezing and extracting the obtained oil seeds to obtain vegetable oil and oil seed meal; performing esterification reaction on the vegetable oil and alcohol to be separated to obtain bio-diesel and crude glycerol; performing cooking treatment on the husks and/or the oil seed meal in the crude glycerol to be separated to obtain oil crude cellulose and glycerol treating liquid; performing microbial fermentation or anaerobic digestion on the oil crude cellulose and the glycerol treating liquid respectively to obtain biological energy sources or bio-based chemicals. The present invention adopts bio-refining type recycling of industrial oil crops to realize efficient co-production of biological energy sources and obviously increase the utilization rate of biomass raw materials in agriculture and forestry.

12 Claims, 4 Drawing Sheets

METHOD FOR CO-PRODUCTION AND PROCESSING OF BIOLOGICAL ENERGY SOURCES BY OIL CROPS

TECHNICAL FIELD

The disclosure herein relates to a method for co-production and processing of biological energy sources by oil crops, and belongs to the technical fields of oleochemical industry and biomass chemical industry.

BACKGROUND

At present, there is a shortage of fuels such as petroleum worldwide, oil prices are gradually rising, petroleum reserves are limited, and the petroleum is not a sustainable resource. Therefore, research on alternative energy is a difficult challenge for researchers around the world. The development and utilization of bio-diesel become an important content of implementation of the sustainable energy strategy in the world, and become a hot spot of new energy development in the world today. The bio-diesel is a fatty acid ester mixture or an alkane mixture obtained by ester exchange reaction or hydrogenation reaction of renewable raw materials such as castor oil, rapeseed oil, recycled cooking oil, animal oil and microbial oil, is a typical environment-friendly "green energy", has the advantages of better fuel performance, high safety, good low temperature starting performance, good lubricating performance and the like, and can be used as a substitute for fossil petroleum.

Based on the analysis of domestic and international research progress on the bio-diesel, inventors find that production of the bio-diesel mainly adopts a chemical synthesis method, and the most important raw materials in the production process are mainly derived from the grease in industrial oil plants, accounting for 70-80% of the production cost. The industrial oil plants refer to energy plants for producing grease or alkane-like raw materials, such as physic nuts, tung trees and Chinese tallow trees, and oil seeds of the industrial oil plants contain rich grease. Due to the specificity of the components of the grease, the grease cannot be eaten and absorbed by the human body and are mainly used for producing raw materials of biological energy sources. In China, woody oil plants have a wide distribution area and rich resources, but the development and research of the woody oil plants are relatively late, so that problems still exist in processing of oil crops. On the one hand, oil processing wastes, such as oil seed meal and oil seed husks, are mainly discarded or incinerated, so that the environment pollution is caused, and the utilization rate of biomass is also reduced. On the other hand, low-grade glycerol produced in the production process of the bio-diesel can be used as a high-boiling-point organic solvent for organic solvent pretreatment of lignocellulose raw materials, and the composition structure of the substrate after pretreatment is changed to contribute to microorganism and enzyme action, thereby being convenient for hydrolysis and saccharification. At present, the high-value utilization processes of industrial oil crop resources have the problems of low raw material utilization rate, high manufacturing cost, complicated manufacturing processes, serious environment pollution, and the like.

In view of the above defects, the inventors actively conduct research and innovation to create a new method for co-production and processing of biological energy sources by oil crops, and the new method has a better industrial utilization value.

SUMMARY

In order to solve the above technical problems, the present invention is directed to a method for co-production and processing of biological energy sources by oil crops. A whole-system bio-refining idea is adopted to realize efficient co-production of multiple bio-based products, thereby increasing the utilization rate of biomass raw materials.

The method for co-production and processing of biological energy sources by oil crops comprises the following steps:

(1) husking and drying oil crop seeds to obtain husks of which the moisture content is 5%-12% and oil seeds of which the moisture content is 30%-55%;

(2) squeezing and extracting the oil seeds obtained in the step (1) to obtain vegetable oil and oil seed meal;

(3) performing esterification reaction on the vegetable oil and alcohol to be separated to obtain bio-diesel and crude glycerol;

(4) performing cooking treatment on the husks and/or the oil seed meal in the crude glycerol to be separated to obtain oil crude cellulose and glycerol treating liquid;

(5) performing microbial fermentation or anaerobic digestion on the oil crude cellulose and glycerol treating liquid obtained in the step (4) respectively to obtain biological energy sources or bio-based chemicals.

Further, the oil crops include one or more of soybeans, rapeseeds, *lindera flavinervia*, pungent litre fruits, *Siberian cocklebur* fruits, physic nuts, Chinese pistache, castor seeds, shinyleaf yellowhorn, *swida wilsoniana*, Chinese tallow trees, oil palms, phoenix trees, tung trees and *euphorbia lathyris*.

Further, in the step (3), the esterification reaction is performed on the vegetable oil and alcohol under the action of a catalyst, wherein the alcohol is methanol or ethanol, and the catalyst is concentrated sulfuric acid or sodium hydroxide.

Further, in the step (3), the mass fraction of the crude glycerol is 20-90%.

Further, in the step (4), the crude glycerol is directly obtained through the step (3) or is obtained through refining treatment of degreasing, pH adjustment, decolorization, ion exchange or concentration processes.

Further, in the step (4), the crude glycerol is directly obtained through the step (3) or is obtained through treatment of degreasing and concentration processes.

Further, in the step (4), the ratio of the mass of the husks or the oil seed meal to the mass of the crude glycerol is (1:6)-(1:30).

Further, in the step (4), the cooking treatment comprises the processes of heating the husks and/or the oil seed meal to 230-270 DEG C. within 10-30 min, keeping the temperature for 10-20 min, and then, reducing the temperature to 70-100 DEG C. The method has the characteristics of normal pressure, high temperature and short time, has low requirements on a treatment device, realizes efficient removal of lignin and hemicellulose components in oil, and produces glycerol self-catalyzed oil crude cellulose.

Further, in the glycerol self-catalyzed oil crude cellulose, the cellulose content is 40-60%, the hemicellulose content is 10-20%, and the lignin content is 10-25%.

Further, in the step (4), the cooking treatment comprises the processes of heating the husks and/or the oil seed meal to 160-200 DEG C. in the presence of alkali, keeping the temperature for 1-20 min, and then, reducing the temperature to 70-100 DEG C. The method has the characteristics of normal pressure, low temperature and short time, has low requirements on the treatment device, realizes efficient removal of lignin and hemicellulose components in oil, and produces glycerol alkali-catalyzed oil crude cellulose.

Further, in the step (4), after cooking treatment, the oil crude cellulose is washed with 1-10 times of room-temperature tap water for 2-5 times, an organic solvent does not need to be used for washing, and the oil crude cellulose is obtained after suction filtration.

Further, in the glycerol alkali-catalyzed oil crude cellulose, the cellulose content is 40-60%, the hemicellulose content is 20-35%, and the lignin content is 5-15%.

The content of each component in the oil crude cellulose obtained by the present invention has important significance for fermentation after-treatment: due to a relatively dense structure of wood fiber, the change of the content of the component indirectly indicates that the structure of the wood fiber is broken, thereby being favorable for subsequent enzymolysis and fermentation after-treatment. In addition, the acetyl in the hemicellulose has an inhibitory effect on the growth of microorganisms in fermentation after-treatment, and the lignin can cause inefficient adsorption of cellulase, thereby reducing the efficiency of enzymatic saccharification of the cellulose. Therefore, control on the content of the hemicellulose and the content of the lignin in a wood fiber substrate has important significance for fermentation after-treatment. In addition, the glycerol cooking treatment in the present invention has stronger selective pertinence, can ensure efficient removal of the lignin and the hemicellulose, and simultaneously has no obvious influence on the cellulose in the oil, thereby indirectly increasing the cellulose content.

Further, the alkali includes one or more of sodium hydroxide, potassium hydroxide and ammonium hydroxide.

Further, the mass of the alkali is 0.05%-1% of the mass of the crude glycerol.

Further, the glycerol treating liquid contains fermentation inhibitors, and the fermentation inhibitors are furfural and 5-hydroxymethylfurfural.

Further, the ratio of the mass of the fermentation inhibitors to the mass of the husks and/or the oil seed meal in the step (4) is (0.01-1):1000.

Further, the temperature is lower during the cooking treatment in the presence of the alkali, and the contents of the fermentation inhibitors are lower than the contents of the fermentation inhibitors under the condition that the cooking treatment is performed without adding the alkali.

Further, in the step (4), the glycerol treating liquid contains glycerol glycoside, glycerol glucoside and glycerol oligoglucoside, and the glycerol glycoside includes one or more of glycerol oligoglycoside, glycerol xyloside and glycerol xylan glycoside.

Further, in the step (5), the biological energy sources or the bio-based chemicals include one or more of hydrogen gas, biogas, ethanol, acetone-butanol, butyric acid, succinic acid, 1,3-propanediol, 2,3-butanediol and microbial oil.

BENEFICIAL EFFECT OF THE INVENTION (1) The present invention adopts the whole-system bio-refining idea and reasonably and fully utilizes the oil crops to produce multiple bio-based products. In the whole processes, industrial oil crops rich in raw materials are adopted, and main components such as oil seed meal, oil seed husks, husks and twigs can be simultaneously utilized, thereby increasing the oil processing benefit and lowering the production cost.

(2) In the prior art, the cooking treatment is performed on the husks and/or the oil seed meal by mainly using low-boiling-point solvents such as water, acetic acid and ethanol which are volatile under the conditions of normal pressure and high temperature, and if a closed container is used, requirements for equipment are high. In the present invention, the glycerol organic solvent which is higher in boiling point and resistant to high temperature is selected for performing the cooking treatment, so that a better treatment effect can be realized. Furthermore, in the present invention, glycerol is directly recovered from bio-diesel wastewater, low-grade glycerol is obtained only by degreasing and concentration treatment, and then, the cooking treatment is performed, thereby reducing energy consumption in the glycerol recovery process.

(3) Compared with the original glycerol organic solvent pretreatment, the present invention can reduce energy consumption by adopting self-catalyzed high-temperature short-time cooking or alkali-catalyzed low-temperature short-time cooking. The cooking method of the present invention can achieve higher removal rates of the lignin and the hemicellulose (the removal rates of the lignin and the hemicellulose can respectively reach 80% and 70%), the retention rate of the cellulose is higher and can be maintained at about 80%, and the enzymolysis efficiency of the treated crude cellulose is higher and reaches about 90%. In addition, the glycerol cooking pretreatment method of the present invention has stronger practicability and applicability for different types of oil crops.

(4) The present invention avoids the conventional hot glycerol-water solution washing and hot water washing and the like, and directly adopts tap water at room temperature for washing, thereby obviously lowering the operation input cost.

(5) The pretreatment process of the present invention hardly produces fermentation inhibitors such as furfural and hydroxymethylfurfural, and the content of the fermentation inhibitors is only about 0.3-0.5%.

(6) The glycerol treating liquid in the present invention contains glycerol glycoside, glycerol glucoside and glycerol oligoglucoside, and the glycerol glycoside includes glycerol oligoglycoside, glycerol xyloside and glycerol xylan glycoside and can be used for biological culture and further fermentation to produce bio-based products. The glycerol is an excellent carbon source for multiple microorganisms, and both glycerol in the pretreatment liquid and residual glycerol on the fiber can be used as a carbon source for subsequent microbial culture.

(7) In the glycerol cooking treatment process of the present invention, under the condition of high temperature or in the presence of alkali, glycerol molecules are linked to monosaccharides (glucose and xylose) or oligosaccharides (cellobiose, xylobiose, and the like) by glycosidic bonds to generate a coupling reaction, thereby forming glycerol glycoside, glycerol glucoside and glycerol oligoglucoside. Glycerol solvents are not used in the prior art, so that the above products cannot be produced in the treatment process. The above products have moisturizing and anti-oxidation functions, can be used as cosmetic additives, and are by-products with high added value in the present invention. The glycerol is often used as an efficient carbon source for microbial fermentation, and is beneficial to the growth of microorganisms. In addition, the glycerol in glycerol glycoside, glycerol glucoside and glycerol oligoglucoside molecules is linked to monosaccharides or oligosaccharides only by glycosidic bonds, and the properties of the glycerol are not changed, so that the glycerol has no inhibitory effect on subsequent fermentation treatment.

(8) The present invention utilizes the glycerol by-product obtained by grease processing and correlates two industries of grease processing of bio-diesel and bio-ethanol and cellulosic biological processing, thereby being favorable for simultaneously promoting the commercialization of the two industries.

DETAILED DESCRIPTION

Figure 1:
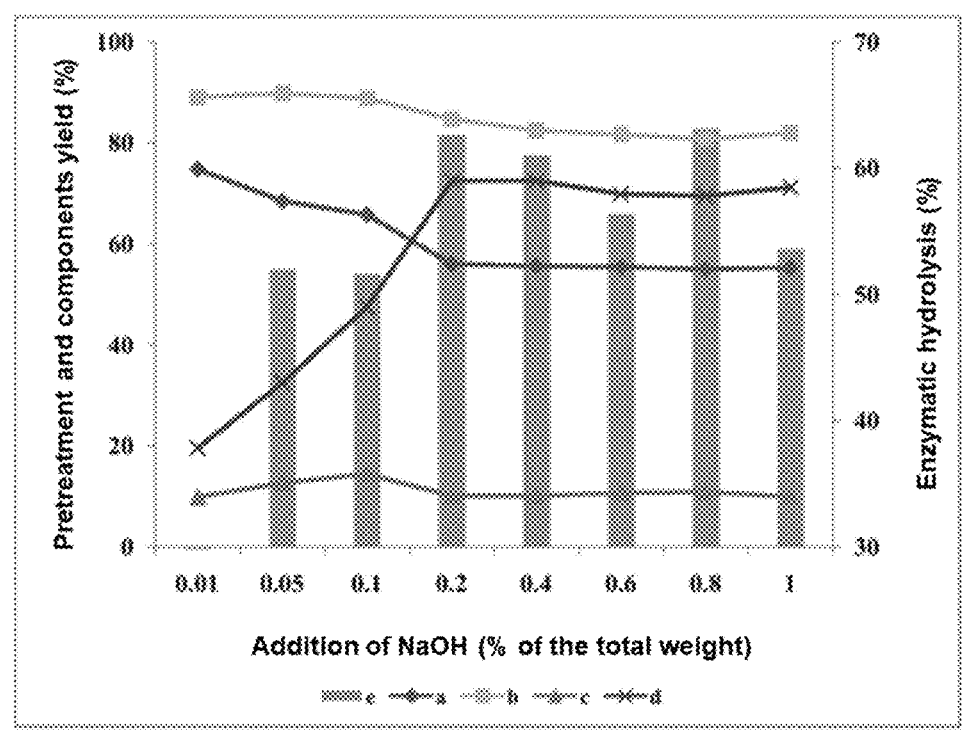
FIG. 1 shows the influence results of different catalyst addition amounts on enzymolysis of castor husks pretreated by glycerol in the present invention.

The detailed description of the present invention is further described by combining the following drawings and examples. The following examples are used to explain the present invention, but are not used to limit the scope of the present invention.

Example 1

Fresh castor fruits are husked by a husker, then 10 kg of castor seeds are taken and dried until the moisture content is 50-55%, control on the moisture content of the castor seeds is favorable for increasing the oil quality and efficiency, a low-temperature cold-pressing technology is used for squeezing and extracting oil, the temperature of a squeezing chamber and the oil outlet temperature are kept at 50 DEG C., and then the obtained castor oil is preserved at 4 DEG C. for later use. Castor seed husks are collected, air-dried until the moisture content is 8-10%, and then pulverized to 5-10 mm.

5 kg of the obtained castor oil and 1 kg of ethanol are taken and mixed uniformly, then the mixture is put in a reactor, simultaneously 50 g of concentrated sulfuric acid as a catalyst is added, and the reaction is performed for 5 h under the conditions that the temperature is 60 DEG C. and the stirring rate is 150 rpm. Then reaction products are transferred into a vacuum rotary evaporator, 4.5 kg of crude bio-diesel is separated at 50-60 DEG C., the non-separated liquid is the crude glycerol, and the crude glycerol is degreased and concentrated to obtain low-grade glycerol of which the content is 70%.

100 g of the pulverized castor seed husks and 1.4 kg of the low-grade glycerol of which the content is 70% are put in a cooking device, the mixture is heated to 250 DEG C. at the stirring rate of 250 rpm, and then the mixture is cooked for 10 min under the condition that the temperature is kept. After the reaction is completed, the reaction products are cooled to 100 DEG C., 300 g of tap water is added, and then, the reaction products are stirred and mixed uniformly and cooled to 50-60 DEG C. Because the glycerol is denser and has lower viscosity, some of the removed lignin is often adhered to the surface of a material and is not completely dissolved in glycerol, boiled water is added to form a glycerol aqueous solution, and simultaneously mechanical stirring is performed to facilitate dissolution of the lignin. Then suction filtration is performed by using a G4 sand core funnel, and elution and suction filtration are performed for 3 times by using tap water (0.4 kg every time), wherein the filter residue is crude cellulose, the mass of the crude cellulose is 66% of the mass of the castor seed husks, the cellulose content is 52%, the removal rates of the hemicellulose and the lignin are respectively 60% and 40%, and the filtrate is the glycerol treating liquid.

50 g of the crude cellulose is taken, 450 g of phosphate buffer (pH 4.8) is added, then 13 mL of cellulase C-Tce2 (120 FPU/mL) is added, pre-enzymolysis is performed for 24 h under the conditions that the stirring rate is 150 rpm and the temperature is 50 DEG C., then 10% Angel *Saccharomyces cerevisiae*, 3 g of ammonium sulfate and 5 mg of potassium dihydrogen phosphate are added, fermentation is performed at 37 DEG C. for 72 h to obtain ethanol, and the yield reaches 43 g/L.

Example 2

Fresh castor fruits are husked by a husker, then 10 kg of castor seeds are taken and dried until the moisture content is 50-55%, control on the moisture content of the castor seeds is favorable for increasing the oil quality and efficiency, a low-temperature cold-pressing technology is used for squeezing and extracting oil, the temperature of a squeezing chamber and the oil outlet temperature are kept at 50 DEG C., and then the obtained castor oil is preserved at 4 DEG C. for later use. Castor seed husks are collected, air-dried until the moisture content is 8-10%, and then pulverized to 5-10 mm.

5 kg of the obtained castor oil and 1 kg of ethanol are taken and mixed uniformly, then the mixture is put in a reactor, simultaneously 50 g of concentrated sulfuric acid as a catalyst is added, and the reaction is performed for 5 h under the conditions that the temperature is 60 DEG C. and the stirring rate is 150 rpm. Then reaction products are transferred into a vacuum rotary evaporator, 4.5 kg of crude bio-diesel is separated at 50-60 DEG C., the non-separated liquid is the crude glycerol, and the crude glycerol is degreased and concentrated to obtain low-grade glycerol of which the content is 70%.

100 g of the pulverized castor seed husks and 1.4 kg of the low-grade glycerol of which the content is 70% are put in a cooking device, 9 g of sodium hydroxide is added, the mixture is heated and stirred at the stirring rate of 250 rpm, and when the temperature raises to 180 DEG C., the mixture is cooked for 10 min under the condition that the temperature is kept. After the reaction is completed, the reaction products are cooled to 100 DEG C., 300 g of tap water is added, and then, the reaction products are stirred and mixed uniformly and cooled to 50-60 DEG C. Suction filtration is performed by using a G4 sand core funnel, and elution and suction filtration are performed for 5 times by using tap water (0.4 kg every time), wherein the filter residue is oil crude cellulose, the mass of the oil crude cellulose is 52% of the mass of the castor seed husks, the cellulose content is 57%, the removal rates of the hemicellulose and the lignin are respectively 40% and 80%, the filtrate is the glycerol treating liquid, the glycerol treating liquid contains glycerol glycoside, glycerol glucoside and glycerol oligoglucoside, and the glycerol glycoside includes glycerol oligoglycoside, glycerol xyloside and glycerol xylan glycoside.

50 g of the oil crude cellulose is taken, 450 g of phosphate buffer (pH 4.8) is added, then 13 mL of cellulase C-Tce2 (120 FPU/mL) is added, pre-enzymolysis is performed for 24 h under the conditions that the stirring rate is 150 rpm and the temperature is 50 DEG C., then 10% Angel S. cerevisiae, 3 g of ammonium sulfate and 5 mg of potassium dihydrogen phosphate are added, fermentation is performed at 37 DEG C. for 72 h to obtain ethanol, and the yield reaches 55 g/L.

By using the method of this example, the addition amount of the catalyst is changed so as to change the enzymolysis yield of the castor husks. FIG. 1 shows the influence of different sodium hydroxide addition amounts on enzymolysis of castor husks pretreated by glycerol under alkali-catalyzed cooking conditions when the cooking temperature is 180 DEG C. and the temperature keeping time is 20 min. In FIG. 1, a represents the pretreatment amount, b represents the cellulose retention rate, c represents the hemicellulose removal rate, d represents the lignin removal rate, and e represents the enzymolysis rate of the bagasse pretreated by glycerol after hydrolysis for 24 h (the substrate concentration is 2%, and the enzyme capacity is 15 FPU/g DM). It can be seen from the figure that with the increase of the addition amount of the alkali, the cellulose retention rate is always kept at about 85%, thereby indicating that the glycerol alkali-catalyzed pretreatment method of the present invention has higher selective pertinence. Furthermore, when the addition amount of the alkali is increased to 2% total system, the lignin removal rate reaches about 80%, and the cellulose enzymolysis rate is maximum. However, the continuous increase in the addition amount of the alkali does not obviously increase the cellulose enzymolysis rate, thereby indicating that in the present invention, because a small amount of alkali is added in glycerol cooking pretreatment, the cooking temperature is reduced, and simultaneously, an efficient pretreatment effect of the castor seed husks can be quickly realized so as to increase the enzymolysis property.

Example 3

Fresh oil palm fruits are husked by a husker, then 10 kg of oil palm seeds are taken and dried until the moisture content is 30-40%, a low-temperature cold-pressing technology is used for squeezing and extracting oil, the temperature of a squeezing chamber and the oil outlet temperature are kept at 50 DEG C., and then the obtained palm oil is preserved at 4 DEG C. for later use. Oil palm seed meal is collected, air-dried until the moisture content is 5-8%, and then pulverized to 7-10 mm.

5 kg of the obtained palm oil and 1 kg of ethanol are taken and mixed uniformly, then the mixture is put in a reactor, simultaneously 30 g of sodium hydroxide as a catalyst is added, and the reaction is performed for 4 h under the conditions that the temperature is 50 DEG C. and the stirring rate is 150 rpm. Then reaction products are transferred into a vacuum rotary evaporator, 4 kg of crude bio-diesel is distilled at 50-60 DEG C., the non-separated liquid is the crude glycerol, and the crude glycerol is degreased and concentrated to obtain low-grade glycerol of which the content is 75%.

500 g of the obtained pulverized oil palm seed meal and 5 kg of 70% ethanol aqueous solution are taken and mixed uniformly, are subjected to ultrasonic-assisted (400 W) treatment in whole processes and are extracted twice for 3 h in a water bath at 70 DEG C., some polyphenol substances in the oil palm seed meal are dissolved in the filtrate, 30 g of polyphenol substances are separated and extracted, 400 g of filter residue is collected, the filter residue is oil seed meal, and the oil seed meal is naturally air-dried and then preserved at 4 DEG C. for later use.

100 g of the pulverized oil seed meal and 1.8 kg of 75% low-grade glycerol solution are put in the cooking device, and the mixture is stirred and heated at the stirring rate of 200 rpm and cooked for 15 min at 240 DEG C. After the reaction is completed, the reaction products are cooled to 100 DEG C., 320 g of tap water is added, and then, the reaction products are mechanically stirred and cooled to 50-60 DEG C. Elution is performed by using tap water, and suction filtration is performed for 3 times by using a G4 sand core funnel (0.4 kg every time), wherein the filter residue is crude cellulose, the mass of the crude cellulose is 55% of the mass of the oil seed meal before reaction, the cellulose content is 54%, the removal rates of the hemicellulose and the lignin are respectively 56% and 48%, and the filtrate is the glycerol treating liquid.

50 g of the crude cellulose is taken, 450 g of phosphate buffer (pH 4.8) is added, then 13 mL of cellulase C-Tce2 (120 FPU/mL) is added, pre-enzymolysis is performed for 24 h under the conditions that the stirring rate is 150 rpm and the temperature is 50 DEG C., then 10% Angel S. cerevisiae, 3 g of ammonium sulfate and 5 mg of potassium dihydrogen phosphate are added, the substrate is intermittently added until the substrate concentration reaches 30% (w/w) during fermentation, fermentation is performed at 37 DEG C. for 72 h to obtain ethanol, and the yield reaches 57 g/L.

Example 4

Fresh oil palm fruits are husked by a husker, then 10 kg of oil palm seeds are taken and dried until the moisture content is 30-40%, a low-temperature cold-pressing technology is used for squeezing and extracting oil, the temperature of a squeezing chamber and the oil outlet temperature are kept at 50 DEG C., and then the obtained palm oil is preserved at 4 DEG C. for later use. Oil palm seed meal is collected, air-dried until the moisture content is 5-8%, and then pulverized to 7-10 mm.

5 kg of the obtained palm oil and 1 kg of ethanol are taken and mixed uniformly, then the mixture is put in a reactor, simultaneously 30 g of sodium hydroxide as a catalyst is added, and the reaction is performed for 4 h under the conditions that the temperature is 50 DEG C. and the stirring rate is 150 rpm. Then reaction products are transferred into a vacuum rotary evaporator, 4 kg of crude bio-diesel is distilled at 50-60 DEG C., the non-separated liquid is the crude glycerol, and the crude glycerol is degreased and concentrated to obtain low-grade glycerol of which the content is 75%.

100 g of the pulverized oil palm seed meal in the example 3 and 1.8 kg of 75% low-grade glycerol solution are put in the cooking device, 12 g of ammonium hydroxide is added, and then the mixture is heated to 200 DEG C., stirred at the stirring rate of 200 rpm and cooked for 6 min at 200 DEG C. After the reaction is completed, the reaction products are cooled to 100 DEG C., 320 g of tap water is added, and then, the reaction products are mechanically stirred and cooled to 50-60 DEG C. Elution is performed by using tap water, and suction filtration is performed for 3 times by using a G4 sand core funnel (0.4 kg every time), wherein the filter residue is crude cellulose, the mass of the crude cellulose is 55% of the mass of the oil palm seed meal before reaction, the cellulose content is 60%, the removal rates of the hemicellulose and the lignin are respectively 70% and 80%, the filtrate is the glycerol treating liquid, the glycerol treating liquid contains glycerol glycoside, glycerol glucoside and glycerol oligoglucoside, and the glycerol glycoside includes glycerol oligoglycoside, glycerol xyloside and glycerol xylan glycoside.

50 g of the crude cellulose is taken, 450 g of phosphate buffer (pH 4.8) is added, then 13 mL of cellulase C-Tce2 (120 FPU/mL) is added, pre-enzymolysis is performed for 24 h under the conditions that the stirring rate is 150 rpm and the temperature is 50 DEG C., then 10% Angel *S. cerevisiae*, 3 g of ammonium sulfate and 5 mg of potassium dihydrogen phosphate are added, the substrate is intermittently added until the substrate concentration reaches 30% (w/w) during fermentation, fermentation is performed at 37 DEG C. for 72 h to obtain ethanol, and the yield reaches 68 g/L.

Example 5

Fresh shinyleaf yellowhorn fruits are husked by a husker, then 10 kg of shinyleaf yellowhorn seeds are taken and dried until the moisture content is 30-40%, a low-temperature cold-pressing technology is used for squeezing and extracting oil, the temperature of a squeezing chamber and the oil outlet temperature are kept at 50 DEG C., and then the obtained shinyleaf yellowhorn seed oil is preserved at 4 DEG C. for later use. Shinyleaf yellowhorn seed meal is collected, air-dried until the moisture content is 8-12%, and then pulverized to 3-10 mm.

5 kg of the obtained shinyleaf yellowhorn seed oil and 1 kg of ethanol are taken and mixed uniformly, then the mixture is put in a reactor, simultaneously 20 g of sodium hydroxide as a catalyst is added, and the reaction is performed for 3 h under the conditions that the temperature is 80 DEG C. and the stirring rate is 200 rpm. Then reaction products are transferred into a vacuum rotary evaporator, 5 kg of crude bio-diesel is distilled at 50-60 DEG C., the non-separated liquid is the crude glycerol, and the crude glycerol is degreased and concentrated to obtain low-grade glycerol of which the content is 83%.

500 g of the obtained pulverized shinyleaf yellowhorn husks and 3.5 kg of 70% ethanol aqueous solution are taken and mixed uniformly, are subjected to ultrasonic-assisted (400 W) treatment in whole processes and are extracted twice for 3 h in a water bath at 70 DEG C., saponin substances in the shinyleaf yellowhorn husks are dissolved in the filtrate, the extraction rate is 0.6 mg/g, 450 g of filter residue is collected, the filter residue includes husks and oil seed meal, and the husks and oil seed meal are naturally air-dried and then preserved at 4 DEG C. for later use.

100 g of the filter residue and 1.4 kg of 83% low-grade glycerol solution are put in the cooking device, 10 g of potassium hydroxide is added, the mixture is heated to 160 DEG C., the temperature is kept for 20 min, and then, the mixture is stirred and cooked at the stirring rate of 250 rpm. After the reaction is completed, the reaction products are cooled to 100 DEG C., 300 g of tap water is slowly added, and then, the reaction products are mechanically stirred and cooled to 50-60 DEG C. Elution is performed by using tap water, and suction filtration is performed for 5 times by using a G4 sand core funnel (0.3 kg every time), wherein the filter residue is oil crude cellulose, the mass of the oil crude cellulose is 63% of the mass of the filter residue before reaction, the cellulose content is 58%, and the removal rates of the hemicellulose and the lignin are respectively 60% and 72%. Cooking liquid and filtrate are collected and mixed uniformly, then the mixture is concentrated to remove moisture to obtain the crude glycerol of which the concentration is 87%, and the crude glycerol can be recycled for 8 times.

50 g of the oil crude cellulose is taken, 450 g of phosphate buffer (pH 4.8) is added, then 15 mL of cellulase C-Tce2 (120 FPU/mL) is added, pre-enzymolysis is performed for 24 h under the conditions that the stirring rate is 150 rpm and the temperature is 50 DEG C., then 15% *S. cerevisiae*, 3 g of ammonium sulfate and 5 mg of potassium dihydrogen phosphate are added, the substrate is intermittently added until the substrate concentration reaches 35% (w/w) during fermentation, simultaneously 10 mL of cellulase C-Tce2 is added, fermentation is performed at 37 DEG C. for 72 h to obtain ethanol, and the yield reaches 75 g/L.

Figure 2:
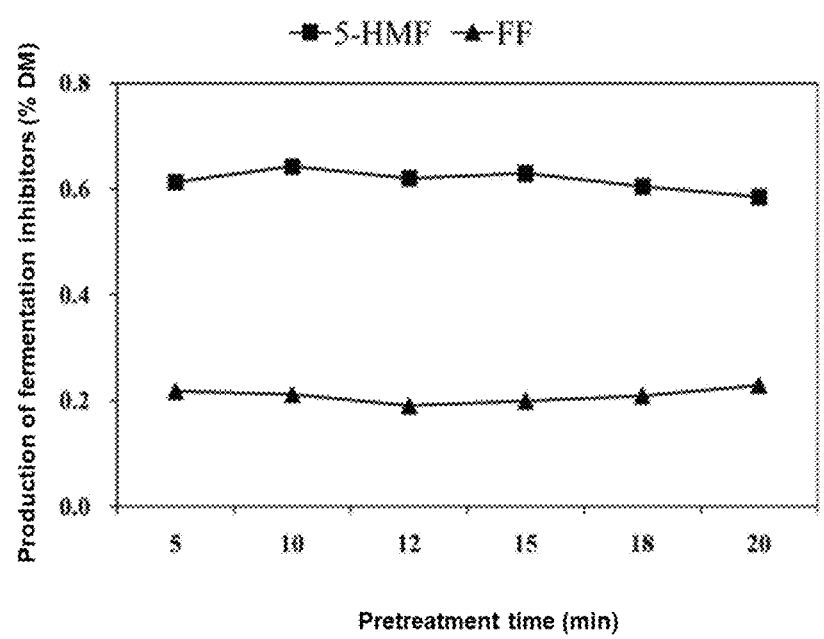
FIG. 2 shows the detection results of the fermentation inhibitors produced by the present invention.

FIG. 2 shows the detection results of the fermentation inhibitors in the glycerol treating liquid of the present invention at different temperature keeping times. In the FIG. 2, 5-HMF represents 5-hydroxymethylfurfural, and FF represents furfural. It can be seen from the FIG. 2 that with the increase of the temperature keeping time, the yield of the inhibitors is always kept at a lower level and is only about 0.3-0.5% of the mass of the shinyleaf yellowhorn husks, thereby indicating that the content of the fermentation inhibitors produced during glycerol cooking pretreatment in the present invention is lower and can be negligible.

Figure 3:
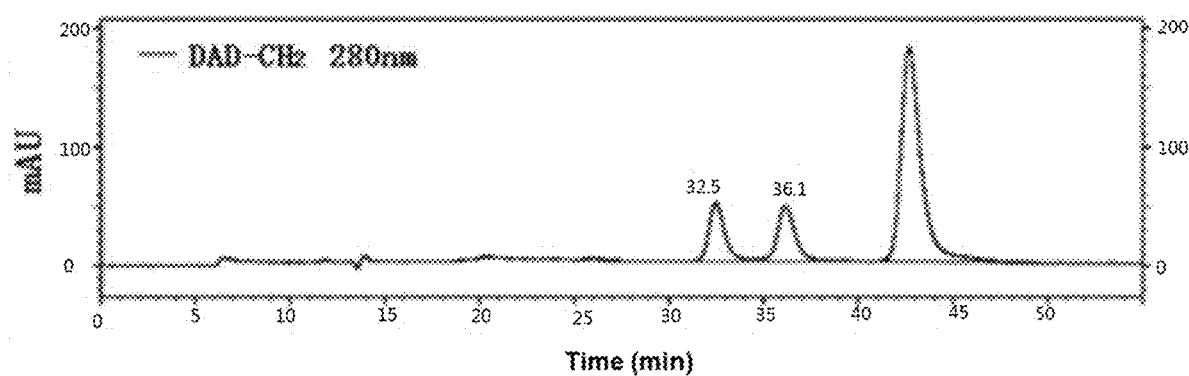
FIG. 3 shows an HPLC (High Performance Liquid Chromatography) test map of the glycerol treating liquid of the present invention.

FIG. 3 shows the HPLC test map of the glycerol treating liquid of the present invention. In the FIG. 3, the peak with the retention time of 32.5 min is glycerol xyloside, and the peak with the retention time of 36.1 min is glycerol dixyloside, thereby indicating that the glycerol xyloside and the glycerol dixyloside with high added value can be produced during glycerol cooking treatment of the present invention. In addition, the peak appearance is relatively obvious, and two peaks have no tailing phenomenon, thereby indicating that the product purity is higher and no similar substances or impurities are produced so as to be favorable for product separation and recovery.

Figure 4:
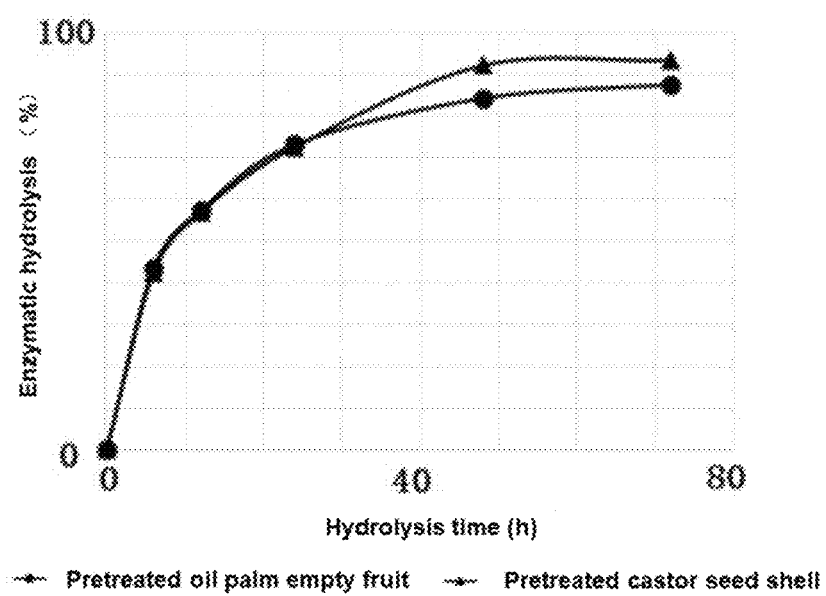
FIG. 4 shows the enzymolysis test results of the crude cellulose obtained by pretreatment on different oil crops through normal-pressure glycerol organic solvents in the present invention.

FIG. 4 shows the enzymolysis test results of the crude cellulose obtained by pretreatment on different oil crops through normal-pressure glycerol organic solvents in the present invention. The enzymolysis conditions are: the solid concentration is 5% (w/v), the enzyme capacity of the cellulase Cellic CTec2 is 4 FPU/g dry substrate, and the citric acid buffer of which the pH value is 4.8 is vibrated and subjected to enzymolysis for 72 h under the conditions that the temperature is 50 DEG C. and the stirring rate is 150 rpm. It can be seen from the FIG. 4 that after different oil crops are pretreated by the glycerol organic solvents, the enzymolysis rates are similar and reach about 90%, and the enzymolysis efficiency is higher, thereby indicating that the lignin and the hemicellulose can be efficiently removed by the invention so as to increase the enzymolysis property, and also indicating that the glycerol cooking pretreatment of the present invention has stronger practicability and applicability for different types of oil crops.

What is claimed is:

1. A method for co-production and processing of biological energy sources by oil crops, wherein the method comprises the following steps:
   (1) husking and drying oil crop seeds to obtain husks which moisture content is 5%-12% and oil seeds which moisture content is 30%-55%;
   (2) squeezing and extracting the oil seeds obtained in the step (1) to obtain vegetable oil and oil seed meal;
   (3) performing esterification reaction on the vegetable oil and alcohol to obtain bio-diesel and crude glycerol, wherein the crude glycerol is obtained by degreasing and concentration treatment;

(4) performing cooking treatment on the husks and/or oil seed meal in the crude glycerol to be separated to obtain oil crude cellulose and glycerol treating liquid, wherein the cooking treatment comprises the processes of heating the husks and/or the oil seed meal to 230-270 DEG C., keeping the temperature for 10-20 min, and then, reducing the temperature to 70-100 DEG C.; or wherein the cooking treatment comprises the processes of heating the husks and/or the oil seed meal to 160-200 DEG C. in the presence of alkali, keeping the temperature for 1-20 min, and then, reducing the temperature to 70-100 DEG C.;

(5) washing the oil crude cellulose obtained in the step (4) with water for 2-5 times, and then, performing microbial fermentation or anaerobic digestion on the washed crude cellulose and glycerol treating liquid respectively to obtain biological energy sources or bio-based chemicals.

2. A method for co-production and processing of biological energy sources by oil crops, wherein the method comprises the following steps:
(1) husking and drying oil crop seeds to obtain husks which moisture content is 5%-12% and oil seeds which moisture content is 30%-55%;
(2) squeezing and extracting the oil seeds obtained in the step (1) to obtain vegetable oil and oil seed meal;
(3) performing esterification reaction on the vegetable oil and alcohol to obtain bio-diesel and crude glycerol;
(4) performing cooking treatment on the husks and/or the oil seed meal in the crude glycerol to be separated to obtain oil crude cellulose and glycerol treating liquid;
(5) performing microbial fermentation or anaerobic digestion on the oil crude cellulose and glycerol treating liquid obtained in the step (4) respectively to obtain biological energy sources or bio-based chemicals.

3. The method for co-production and processing of biological energy sources by oil crops according to claim 2, wherein in the step (4), the cooking treatment comprises the processes of heating the husks and/or the oil seed meal to 230-270 DEG C., keeping the temperature for 10-20 min, and then, reducing the temperature to 70-100 DEG C.

4. The method for co-production and processing of biological energy sources by oil crops according to claim 2, wherein in the step (4), the cooking treatment comprises the processes of heating the husks and/or the oil seed meal to 160-200 DEG C. in the presence of alkali, keeping the temperature for 1-20 min, and then, reducing the temperature to 70-100 DEG C.

5. The method for co-production and processing of biological energy sources by oil crops according to claim 4, wherein the alkali comprises one or more of sodium hydroxide, potassium hydroxide and ammonium hydroxide.

6. The method for co-production and processing of biological energy sources by oil crops according to claim 4, wherein the mass of the alkali is 0.05%-1% of the mass of the crude glycerol.

7. The method for co-production and processing of biological energy sources by oil crops according to claim 2, wherein in the step (4), after cooking treatment, the oil crude cellulose is washed with water for 2-5 times.

8. The method for co-production and processing of biological energy sources by oil crops according to claim 2, wherein the oil crops comprise one or more of soybeans, rapeseeds, *Lindera flavinervia*, pungent litre fruits, *Siberian cocklebur* fruits, physic nuts, Chinese pistache, castor seeds, shinyleaf yellowhorn, *Swida wilsoniana*, Chinese tallow trees, oil palms, phoenix trees, tung trees and *Euphorbia lathyris*.

9. The method for co-production and processing of biological energy sources by oil crops according to claim 2, wherein in the step (4), the glycerol treating liquid comprises fermentation inhibitors; and wherein the fermentation inhibitors are furfural and 5-hydroxymethylfurfural.

10. The method for co-production and processing of biological energy sources by oil crops according to claim 9, wherein the ratio of the mass of the fermentation inhibitors to the mass of the husks and/or the oil seed meal in the step (4) is (0.01:1000)-(1:1000).

11. The method for co-production and processing of biological energy sources by oil crops according to claim 2, wherein in the step (4), the glycerol treating liquid comprises glycerol glycoside, glycerol glucoside and glycerol oligoglucoside; and wherein the glycerol glycoside comprises one or more of glycerol oligoglycoside, glycerol xyloside and glycerol xylan glycoside.

12. The method for co-production and processing of biological energy sources by oil crops according to claim 2, wherein in the step (5), the biological energy sources or the bio-based chemicals comprise one or more of hydrogen gas, biogas, ethanol, acetone-butanol, butyric acid, succinic acid, 1,3-propanediol, 2,3-butanediol and microbial oil.

* * * * *